US007286227B2

(12) United States Patent
Zhou et al.

(10) Patent No.: US 7,286,227 B2
(45) Date of Patent: Oct. 23, 2007

(54) METHOD AND SYSTEM FOR REMOVING THE EFFECTS OF CORNEAL BIREFRINGENCE FROM A POLARIMETRIC IMAGE OF THE RETINA

(75) Inventors: Qienyuan Zhou, Del Mar, CA (US); Xiangrun Huang, Miami, FL (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 0 days.

(21) Appl. No.: 10/260,481

(22) Filed: Sep. 30, 2002

(65) Prior Publication Data

US 2004/0061834 A1 Apr. 1, 2004

(51) Int. Cl.
*A61B 3/10* (2006.01)
*G01J 4/00* (2006.01)

(52) U.S. Cl. ........................... 356/367; 351/215
(58) Field of Classification Search ............... 351/205, 351/206, 215, 221; 356/364–370, 337, 342; 600/310, 318–321, 407, 473, 476, 558
See application file for complete search history.

(56) References Cited

U.S. PATENT DOCUMENTS

| | | | | |
|---|---|---|---|---|
| 5,303,709 | A | 4/1994 | Dreher et al. | 128/665 |
| 5,787,890 | A | 8/1998 | Reiter et al. | 128/665 |
| 5,920,373 | A | 7/1999 | Bille | 351/212 |
| 6,112,114 | A | 8/2000 | Dreher | 600/476 |
| 6,137,585 | A | 10/2000 | Hitzenberger et al. | 356/484 |
| 6,356,036 | B1 * | 3/2002 | Zhou | 351/215 |
| 6,704,106 | B2 * | 3/2004 | Anderson et al. | 356/367 |

OTHER PUBLICATIONS

Bueno, Juan M. & Vargas–Martin, Fernando "Measurements of the Corneal Birefringence with a Liquid–Crystal Imaging Polariscope." *Applied Optics*, vol. 41, No. 1, Jan. 1, 2002.
Bueno, Juan M. and Campbell, Melanie C.W. "Confocal Scanning Laser Ophthalmoscopy Improvement by Use of Mueller–Matrix Polarimetry." *Optical Society of America*, vol. 27, No. 10, May 15, 2002.
Bueno, Juan M. & Jaronski, Jaroslaw "Spatially Resolved Polarization Properties for In Vitro Corneas." in *Ophthal. Physiol. Opt.*, vol. 21, pp. 384–392, 2001.
Bueno, Juan M. "Depolarization Effects in the Human Eye." in *Vision Research* 41 (2001) ppg. 2687–2696.
Bueno, Juan M. "Indices of Linear Polarization for an Optical System." *Journal of Optics A; Pure and Applied Optics*, vol. 3(2001) ppg. 470–476.
Bagga, H., Greenfield, D.S., Knighton, R.W. "Scanning Laser Polarimetry With Variable Corneal Compensation in Eyes with Macular Pathology" University of Miami School of medicine, Bascom Palmer Eye Institute, Miami, Fl., Presentation No. 250; Poster Board No. B225 (May 5, 2002).
Bueno, Juan M. "Polarimetry Using Liquid–Crystal Variable Retarders: Theory and Calibration." *Journal of Opthamology*, 2 (2000) 216–222.
Bueno, Juan M. and Artal, Pablo "Douple–pass Imaging Polarimetry in the Human Eye." *Optics Letters*, vol. 24, No. 1, Jan. 1, 1999.
Knighton, R.W.; Huang, X–R; Greenfield, D.S.; "Analytical Model of Scanning Laser Polarimetry for Retinal Nerve Fiber Layer Assessment" *Investigative Opthalmological & Visual Science*, vol. 43, No. 2, Feb. 2002 (Feb. 2002), pp. 383–392.
Bueno, J.M. et al.; "Double–Pass Imaging Polarimetry in the Human Eye" *Optics Letters, Optical Society of America* Washington, U.S. vol. 24, No. 1, 1999, pp. 64–66.

* cited by examiner

*Primary Examiner*—Brian L. Casler
*Assistant Examiner*—John R Sanders
(74) *Attorney, Agent, or Firm*—Stallman & Pollock LLP

(57) ABSTRACT

A scanning laser polarimetry (SLP) system that measures in vivo retinal nerve fiber layer (RNFL) retardance ($\delta_N$, $\theta_N$) in a single measurement without a variable corneal compensator (VCC). The diagnostic signal is biased so that the detected RNFL retardance orientation angles are sufficiently similar at adjacent pixels in the retinal polarimetric image to permit resolution of the orientation angle ambiguity in a single polarimetric image without repeating the measurement at another signal polarization state. With a simple bias retarder, the effects of anterior segment retardance ($\delta_C$, $\theta_C$) can be removed from a single polarimetric image of the retina without a VCC. Alternatively, from two single polarimetric images obtained at two different bias retarder positions, the anterior segment retardance magnitude $\delta_C$ and orientation $\theta_C$ and the RNFL retardance magnitude $\delta_N$ and orientation $\theta_N$ can all be determined from the peripapillary RNFL image region alone.

20 Claims, 6 Drawing Sheets

METHOD AND SYSTEM FOR REMOVING THE EFFECTS OF CORNEAL BIREFRINGENCE FROM A POLARIMETRIC IMAGE OF THE RETINA

CROSS-REFERENCES TO RELATED APPLICATIONS

This application is related by common inventorship and subject matter to the commonly-assigned patent application Ser. No. 10/160,808 filed on May 31, 2002, U.S. Pat. No. 6,704,106 entitled A METHOD AND SYSTEM FOR CANCELING SYSTEM RETARDANCE ERROR IN AN OPHTHALMOLOGICAL POLARIMETER and entirely incorporated herein by this reference.

BACKGROUND OF THE INVENTION

1. Field of the Invention

This invention relates generally to ophthalmological polarimeter systems for measuring retinal layer retardances and more particularly to an ophthalmological system for removing the effects of anterior segment birefringence from a polarimetric image of the retina.

2. Description of the Related Art

Knowing the optical characteristics of the cornea is very useful to the ophthalmologist. For example, Josef Bille describes a method and apparatus for determining optical characteristics of a cornea in U.S. Pat. No. 5,920,373. Bille describes an ellipsometer for generating a laser beam signal in a scanning tomography unit, which establishes a precise focal plane for birefringence measurements of elements in the human eye. Bille's method is procedurally and computationally intensive. Once the ellipsometer is properly focused, the laser beam emanating from the ellipsometer is selectively polarized to sequentially obtain sixteen different readings from a point in the plane of focus. These sixteen readings are then collectively used as contributions to a measurement of the birefringent property of the material at the point of focus. This process must be repeated to obtain measurements of the birefringent properties at all other image points in the plane of focus and the entire imaging procedure must be repeated to obtain the polarimetric image properties at another plane of focus.

Other practitioners concerned with corneal birefringence have also proposed various polarimetric techniques. For example, some have demonstrated the usefulness of Mueller-matrix polarimetry to assess the polarization properties of the eye.

As is well-known in the art, a general polarimeter may be used to measure the polarization properties of any optical signal, which may be expressed in terms of, for example, the Stokes vector S, which includes four components [Sj] (j=0, 1, 2, 3) that completely characterize the polarization state of an optical signal. The Stokes vector S is conventionally expressed as a four-component column vector $$S = \begin{bmatrix} I \\ Q \\ U \\ V \end{bmatrix}. \quad \text{[Eqn. 1]}$$

Components [Sj] may be characterized as simple combinations of intensity outputs from various combinations of linear or circular polarizers, where I is the total optical signal intensity, Q is the intensity difference between the horizontal and vertical linearly-polarized optical signal components, U is the intensity difference between the linearly-polarized optical signal components oriented at ±45 degrees, and V is the intensity difference between the right and left circularly-polarized optical signal components. The polarization state of any electromagnetic signal, such as a light beam, is entirely described by the four-element Stokes column vector S. Ignoring signal intensity, any Stokes vector can be located on a so-called Poincaré sphere defined on the orthogonal Q, U and V axes in the manner well-known in the art.

The Mueller matrix M for a system is conventionally expressed as a 4 by 4 matrix with real elements [Mij] (i, J =0, 1, 2, 3) that contain sufficient information to describe all polarization properties of the system. Any change produced by an optical system to the polarization state $S_I$ of an incoming optical signal may be expressed as a linear transformation ($S_O$=M $S_I$) of the Stokes vector for the incoming optical signal in a four-dimensional space, where M is the Mueller matrix for the optical system and $S_O$ is the Stokes vector for the outgoing optical signal:

$$S_O = \begin{bmatrix} I_O \\ Q_O \\ U_O \\ V_O \end{bmatrix} = \begin{bmatrix} M_{00} & M_{01} & M_{02} & M_{03} \\ M_{10} & M_{11} & M_{12} & M_{13} \\ M_{20} & M_{21} & M_{22} & M_{23} \\ M_{30} & M_{31} & M_{32} & M_{33} \end{bmatrix} \begin{bmatrix} I_I \\ Q_I \\ U_I \\ V_I \end{bmatrix} \quad \text{[Eqn. 2]}$$

The usual parameters characterizing the polarizing properties of the optical system, such as retardance and reflectivity, do not appear explicitly and certain polar decomposition theorems are required to obtain physically-useful information from the Mueller matrix elements. Generally, the $M_{00}$ element represents the intensity profile of the emergent beam when non-polarized light is entering the system. Elements $M_{01}$, $M_{02}$ and $M_{03}$ describe the attenuation between two orthogonal polarization states, which is often denominated the diattenuation or dichroism (D) of the optical system. Elements $M_{10}$, $M_{20}$ and $M_{30}$ characterize the possibility of increasing the degree of polarization of a non-polarized incident light, which is often denominated the polarizance (P) of the optical system. All Mueller matrix elements contribute to the calculation of the degree of polarization (DOP) of the optical system and the lower 3 by 3 sub-matrix elements [Mij] (i, j=1, 2, 3) alone contain information on the retardation (also denominated retardance) introduced by system birefringent structures. DOP, D and P range in value from 0 to 1 and may be expressed as closed-form functions of the appropriate Mueller matrix elements.

The birefringence of each of the various segments in the eye is assumed to be equivalent to a linear retarder and is usually expressed in terms of the retardance magnitude δ in radians (2π times the product of retarder delay time and signal frequency) and the fast-axis orientation angle θ for the segment in radians (with respect to an arbitrary horizontal basis). A linear retarder may be described by a sixteen-element Mueller matrix written in terms of retardance δ and fast-axis angle θ as follows:

$$M(\delta, \rho) = \begin{bmatrix} \alpha & 0 & 0 & 0 \\ 0 & c^2 + ks^2 & sc(1-k) & -sx \\ 0 & sc(1-k) & c^2 + ks^2 & cx \\ 0 & sx & -cx & k \end{bmatrix} \quad \text{[Eqn. 3]}$$

where c=cos 2θ, s=sin 2θ, k=cos δ, x=sin δ, and α=amplitude attenuation. Note that the nine sub-matrix elements [Mij] (i, j=1, 2, 3) are sufficient to describe the polarization properties of a linear retarder. Using Eqn. 3, the total retardance $\delta_T$ of a sequence of two retarders with respective retardances $\delta_1$, $\delta_2$ can be shown to vary according to the relationship between the fast-axis orientation angles $\theta_1$, $\theta_2$ of the two retarders as follows:

$$\cos \delta_T = \cos \delta_1 \cos \delta_2 - \sin \delta_1 \sin \delta_2 \cos 2(\theta_2 - \theta_1) \quad \text{[Eqn 4]}$$

Note that $\delta_T = 0$ when $\cos \delta_1 \cos \delta_2 = 1 + \sin \delta_1 \cos \delta_2 \cos 2(\theta_2 - \theta_1)$, showing to "cancel" a retardance with another properly-oriented linear retarder. Two identical aligned retarders of magnitude $\delta$ (or two signal passes through a single linear retarder) is, by Eqn. 4, equivalent to a single retarder having retardance magnitude $2\delta$, so that $$M(\delta, \theta)M(\delta, \theta) = M(2\delta, \theta) \quad \text{[Eqn. 5]}$$

Because the cornea is an important optical segment of the eye, the properties of in vitro mammalian corneas have been studied by practitioners in the ophthalmological art for several different purposes. For example, Bueno et al. (J. M. Bueno and J. Jaronski, "Spatially Resolved Polarization Properties for in vitro Corneas," *Ophthal. Physiol. Opt.*, Vol 21, pp 384–92, 2001) discuss using a Mueller-matrix imaging polarimeter in transmission mode to obtain spatially-resolved images (bitmaps) of each of the sixteen Mueller matrix elements over the cornea sample. Bueno et al. dispose a corneal sample between a polarization-state generator (PSG) and a polarization-state analyzer (PSA) each including at least one quarter-wave plate. By rotating the PSG and PSA quarter-wave plates in turn to one of four independent angular positions, sixteen independent measurements can be obtained for each pixel in a scanned image, thereby providing information sufficient for computing sixteen Mueller matrix component images of the corneal sample. A related reflective-mode procedure is employed to obtain the Mueller matrix component images of a reflective sample. Bueno et al. observe that their arrangement using sixteen independent combinations of PSG and PSA settings allows direct computation of the Mueller matrix by matrix-inversion, thereby eliminating the usual requirement for a Fourier analysis of the detected optical signal. As expected from earlier studies, Bueno et al. found the in vitro corneal retardance characteristics to vary monotonically from center to edge.

The properties of in vivo human corneas have also been studied by several practitioners in the ophthalmological art. For example, Bueno et al. (J. Bueno and P. Artal, "Double-Pass Imaging Polarimetry in the Human Eye," *Optics Letters*, Vol. 24, No. 1, Jan. 1, 1999) describes a Mueller-matrix polarimeter disposed in a double-pass setup that includes two liquid-crystal variable retarders (LCVRs) and a slow scan charge-coupled device (CCD) camera. To obtain a complete set of the polarization characteristics of the in vivo human eye, three independent LCVR voltages are used to obtain nine independent polarimetric combinations. A removable quarter-wave plate is added in each leg of the polarimeter to introduce the "fourth state" necessary to complete the measurements necessary to populate the sixteen-element Mueller matrix. Later, Bueno (J. Bueno, "Polarimetry Using Liquid-Crystal Variable Retarders: Theory and Calibration," *J. Opt. A: Pure Appl. Opt.*, Vol. 2, pp. 216–22, January 2000) describes the double-pass apparatus in more detail, including a requirement for independent calibration of each LCVR to ensure accuracy of the final Mueller matrix element images.

Bueno suggests a similar Mueller matrix polarimetry technique for examining the depolarizing properties of in vivo human corneas (Bueno, "Depolarization Effects in the Human Eye," *Vision Research*, Vol. 41, pp. 2687–96, 2001), noting that the human eye presents a slight polarizing power mainly because of the presence of both circular birefringence and dichroism in the anterior segments including the cornea. Two independent rotatable quarter-wave plates (PSG and PSA) are each rotated among four positions to create the sixteen independent optical measurements necessary and sufficient to compute the Mueller matrix component images. Bueno (J. Bueno, "Indices of Linear Polarization for an Optical System," *Journal of Optics A:*, Vol. 3, pp. 470–76, October 2001) also defines a pair of direct and reverse linear polarization indices to quantify deviation of the measured Mueller matrix from a perfectly linear polarizer. Nine of the Mueller matrix elements are sufficient to determine this pair of linear polarization indices.

More recently, Bueno et al. (J. Bueno and F. Vargas-Martin, "Measurements of the Corneal Birefringence With a Liquid-Crystal Imaging Polariscope," *Applied Optics*, Vol. 41, No. 1, Jan. 1, 2002) provide more results of human in vivo cornea studies, suggesting that the measured variation of retardance across the pupil may result from combined effects of corneal and retinal birefringence, which are not easily separated in the living human eye. Bueno et al. use Mueller-matrix polarimetry to examine optical signals reflected from the iris. They measure a second Mueller matrix modeling the iris and use it to distinguish the iris effects from the corneal retardance data, thereby enhancing isolation of corneal birefringence from retinal birefringence. Later, Bueno et al. (J. Bueno and M. Campbell, "Confocal Scanning Laser Ophthalmolscopy Improvement by Use of Mueller-Matrix Polarimetry," *Optics Letters*, Vo. 27, No. 10, May 15, 2002) suggest using the same sixteen-element Mueller-matrix polarimetry technique for confocal microscopy and specular reflection analysis.

The scanning laser polarimeter (SLP) art is described in the commonly-assigned U.S. Pat. Nos. 5,303,709, 5,787, 890, 6,112,114, and 6,137,585, all of which are entirely incorporated herein by reference. The SLP is a diagnostic ophthalmological device that determines the thickness of the retinal nerve fiber layer (RNFL) by measuring the retardance magnitude and orientation angle ($\delta_N$, $\theta_N$) of polarized light double-passing through the RNFL layer and correlating RNFL thickness to the measured retardance ($\delta_N$, $\theta_N$) according to biological principles. In the eye, the anterior segment birefringence includes the combined birefringence of the cornea and the crystalline lens, and the posterior segment includes regions at the fundus. The array of nerve fibers converging from all parts of the retina to the optic nerve head is characteristically unique. Many retinal nerve fibers diverge from the fovea and curve around to converge to the optic nerve head. Within the central four or five degrees of visual field, in the fovea, other fibers, called Henle fibers, are arranged radially, like the spokes of a wheel. Both the retinal nerve fibers and the Henle fibers have "form birefringence," with the optic axis of the birefringence parallel to the direction of the fiber. The Henle fiber retardance magnitude varies little over the normal macula.

The SLP system must segregate the effects of anterior birefringence ($\delta_C$, $\theta_C$) from the data to obtain the desired RNFL retardance ($\delta_N$, $\theta_N$) and the SLP art includes several useful methods for doing so. One method described in the above-cited patents employs a predetermined retarder ($\delta_F$, $\theta_F$) in the optical path to cancel a predetermined anterior segment retardance ($\delta_C$, $\theta_C$) in the manner suggested by Eqn. 4 above. The SLP polarimetric image provides values for the measured total retardance magnitude $\delta_T$ and orientation angle $\theta_T$, but a single polarimetric image scan cannot resolve whether the measured orientation angle $\theta_T$ represents the fast-axis or the slow-axis of the total birefringence of the measured system. To resolve this "fast or slow axis ambiguity" this SLP method rotates a fixed retarder to a second orientation to obtain a second independent polarimetric scan image and determine whether the orientation measurement is the fast or slow axis, With a properly adjusted VCC, this produces a retardance magnitude $\delta_N$ scan image and an orientation axis $\theta_N$ scan image. But with a fixed anterior segment correction, the RNFL thickness measurements may be subject to significant errors arising from uncompensated anterior segment birefringence. For example, the orientation angle of corneal birefringence is known to vary among individuals, sometimes by a large angle, which may tend to mask some of the RNFL characteristics useful in identifying and diagnosing the subtle effects of certain disease processes. Another described method overcomes this disadvantage by first measuring an anterior segment retardance ($\delta_C$, $\theta_C$) using standard confocal polarimetry to isolate and analyze reflections from the posterior surface of the crystalline lens and then adjusting a variable corneal compensator (VCC) to approximate the retardance magnitude $\delta_F$ and fast-axis angle $\theta_F$ values necessary to cancel the measured retardance ($\delta_C$, $\theta_C$) in the manner suggested by Eqn. 4 above.

The commonly-assigned U.S. Pat. No. 6,356,036 B1, entirely incorporated herein by reference, discloses an improved SLP that uses post-measurement analysis of macula scan images to determine the compensation ($\delta_F$, $\theta_F$) necessary to cancel anterior segment retardance ($\delta_C$, $\theta_C$). With VCC retardance set to zero, a first SLP image is made to produce magnitude $\delta_T$ and orientation $\theta_T$ image maps of the combined anterior and posterior segment retardance over the RNFL and macula regions. An annular profile of the retardance magnitude $\delta_T$ is computed from an annular locus of pixels (image points) centered on the fovea in the $\delta_T$ image of the macula (Henle fiber layer). A single retardance value ($\delta_C$, $\theta_C$), representing the average anterior segment retardance (over the scan region of 2 mm or so) is derived from this annular retardance profile by assuming that the Henle fiber layer retardance ($\delta_H$, $\theta_H$) has a fixed magnitude $\delta_H$ and a radially-disposed slow-axis orientation ($\theta_H+\pi/2$). The VCC is then set to the retardance ($\delta_F$, $\theta_F$) necessary to cancel the calculated anterior segment retardance ($\delta_C$, $\theta_C$) and a second pair of SLP image scans is made to produce a retardance magnitude $\delta_N$ scan image and an orientation axis $\theta_N$ scan image. This SLP procedure improves accuracy by using adjustable compensation and by using the Henle layer in the macula (instead of the posterior lens surface) as a reference reflection surface for measuring a ($\delta_C$, $\theta_C$) value representing anterior segment birefringence. This procedure assumes a healthy macula with no pathology affecting the normal optical characteristics of the Henle fiber layer.

The above-cited patent application (Ser. No. 10/160,808 filed on May 31, 2002) discloses an improved SLP incorporating a residual retardance canceling system that reduces another important source of RNFL retardance measurement error by canceling the effects of residual system birefringence in the diagnostic path.

Although these SLP improvements have eliminated much of the RNFL measurement error arising from uncompensated birefringence in the measurement path, several disadvantages remain. For example, the anterior segment retardance ($\delta_C$, $\theta_C$) must first be measured before it can be later canceled. And the anterior segment cancellation requires the introduction or adjustment of a compensating linear retarder in the optical measurement path before repeating the RNFL imaging procedure. Moreover, each SLP retardance ($\delta$ and $\theta$) measurement requires two independent measurements to resolve the retardance angle $\theta$ ambiguity. A first pair of scan images is needed to estimate $\delta_C$ and $\theta_C$ for the anterior segment. The VCC must then be set to cancel $\delta_C$ and $\theta_C$ before making the second pair of scan images needed to obtain RNFL retardance $\delta_N$ and $\theta_N$, from which the desired RNFL thickness data are finally obtained. While this procedure is more efficient than the sixteen measurements required to populate an entire Mueller matrix for the RNFL image, it disadvantageously requires two complete double-scans of the retina separated by an intermediate VCC readjustment.

There is accordingly a clearly-felt need in the art for a method and system that can measure RNFL features with fewer scans for improved speed and efficiency and with the accuracy necessary for automated classification of the retinal effects of disease processes in the earlier stages. There is a particular need for a SLP system that requires neither an independent set of anterior segment retardance measurements nor the readjustment of a VCC. The unresolved problems and deficiencies are clearly felt in the art and are solved by this invention in the manner described below.

SUMMARY OF THE INVENTION

This invention solves the above problems for the first time by introducing a scanning laser polarimetry (SLP) method that measures retinal nerve fiber layer (RNFL) retardance in a single scan image without a variable corneal compensator (VCC). The method of this invention arises in part from the unexpectedly advantageous observation that the similarity of RNFL retardance axis orientations at adjacent points in the retina can be used to eliminate the orientation angle ambiguity normally present in a single polarimetric image without repeating the measurement at another signal polarization state. This invention also eliminates the need for a variable corneal compensator (VCC) element. For example, with a simple bias retarder, the effects of anterior segment retardance ($\delta_C$, $\theta_C$) may be removed from a single polarimetric image of the retina without a VCC by the method of this invention. Using a single polarimetric image is particularly advantageous for simplicity and reduced registration error. Alternatively, from two single retinal scan images with a bias retarder set in two positions, the anterior segment retardance magnitude $\delta_C$ and orientation $\theta_C$ and the RNFL retardance magnitude $\delta_N$ and orientation $\theta_N$ can all be determined from the peripapillary RNFL region alone without considering the macular region according to an alternative method of this invention.

It is a purpose of this invention to provide a SLP system for measuring RNFL retardance quickly without corneal compensation. It is an advantage of the system of this invention that RNFL retardance may be determined with a single scan image using only a bias retarder. It is another advantage of the system of this invention that a single retinal scan of the macula and RNFL is sufficient to resolve orientation angle ambiguity and eliminate anterior segment birefringence effects from the RNFL scan image without corneal compensation.

It is another purpose of this invention to provide a SLP system for measuring RNFL retardance using a double scan of the RNFL region alone without corneal compensation. It is an advantage of the system of this invention that the anterior segment retardance magnitude $\delta_C$ and orientation $\theta_C$ and the RNFL retardance magnitude $\delta_N$ and orientation $\theta_N$ can all be determined from the peripapillary RNFL region of two scan images with a bias retarder set in two positions. It is another advantage of the system of this invention that the macular region of two scan images with a bias retarder set in two positions may alternatively be used to determine the anterior segment retardance magnitude $\delta_C$ and orientation $\theta_C$ for elimination from the peripapillary RNFL region of the images.

In one aspect, the invention is a method for analyzing the birefringence of a retinal structure of an eye including the steps of (a) producing a first polarimetric image of the retinal structure having a plurality of pixels $\{S(\delta_T, \theta_T)\}$ each representing a measured retardance magnitude $\delta_T$ and orientation angle $\theta_T$, (b) determining the fast axes of the pixel retardance angles $\{\theta_T\}$ corresponding to a biological feature of the retinal structure in the first polarimetric image, (c) determining anterior segment retardance magnitude $\delta_C$ and orientation $\theta_C$ values corresponding to the variation of the retardance magnitude $\delta_T$ over an annular region of the first polarimetric image, and (d) computing a second polarimetric image of the retinal structure having a plurality of pixels $\{S(\delta_N, \theta_N)\}$ each corresponding to a first polarimetric image pixel $S(\delta_T, \theta_T)$ from which the effects of the anterior segment retardance are removed.

In another aspect, the invention is a method for analyzing the birefringence of a retinal structure of an eye including the steps of (a) producing a first polarimetric image of the retinal structure each having a plurality of pixels $\{S(\delta_{T1}, \theta_{T1})\}$ each representing a measured retardance magnitude $\delta_{T1}$, and orientation angle $\theta_{T1}$, (b) producing a second polarimetric image of the retinal structure having a plurality of pixels $\{S(\delta_{T2}, \theta_{T2})\}$ each representing a measured retardance magnitude $\delta_{T2}$ and orientation angle $\theta_{T2}$, (c) computing, for a plurality of pixels $\{S_i\}$ from the first and second polarimetric images, anterior segment retardance magnitude $\delta_C$ and orientation $\theta_C$ values that provide a minimum least-squares error fit of a Mueller equation, and (d) computing a third polarimetric image of the retinal structure having pixels $\{S(\delta_N, \theta_N)\}$ each corresponding to a first or second polarimetric image pixel $S(\delta_T, \theta_T)$ from which the effects of the anterior segment retardance are removed.

In an exemplary embodiment, the invention is an ophthalmological system for analyzing the birefringence of a retinal structure of an eye having an anterior segment and a pupil, including a scanning laser polarimeter for producing a first polarimetric image of the retinal structure having a plurality of pixels $\{S(\delta_T, \theta_T)\}$ each representing a measured retardance magnitude $\delta_T$ and orientation angle $\theta_T$, first processor means for determining the fast axes of the pixel retardance angles $\{\theta_T\}$ corresponding to a biological feature of the retinal structure in the first polarimetric image, second processor means for determining anterior segment retardance magnitude $\delta_C$ and orientation $\theta_C$ values corresponding to the variation of the retardance magnitude $\delta_T$ over an annular region of the first polarimetric image, and third processor means for computing a second polarimetric image of the retinal structure having a plurality of pixels $\{S(\delta_N, \theta_N)\}$ each corresponding to a first polarimetric image pixel $S(\delta_T, \theta_T)$ from which the effects of the anterior segment retardance are removed.

The foregoing, together with other objects, features and advantages of this invention, can be better appreciated with reference to the following specification, claims and the accompanying drawing.

BRIEF DESCRIPTION OF THE DRAWINGS

For a more complete understanding of this invention, reference is now made to the following detailed description of the embodiments as illustrated in the accompanying drawing, in which like reference designations represent like features throughout the several views and wherein.

DETAILED DESCRIPTION OF THE EMBODIMENTS

Figure 1B:
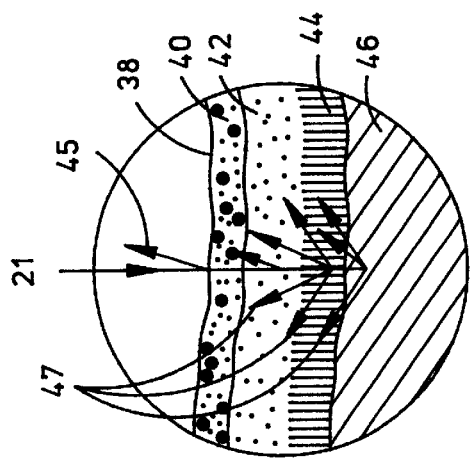
FIG. 1B is a cross-sectional view of the retina along line 1B—1B in FIG. 1A.
Figure 1A:
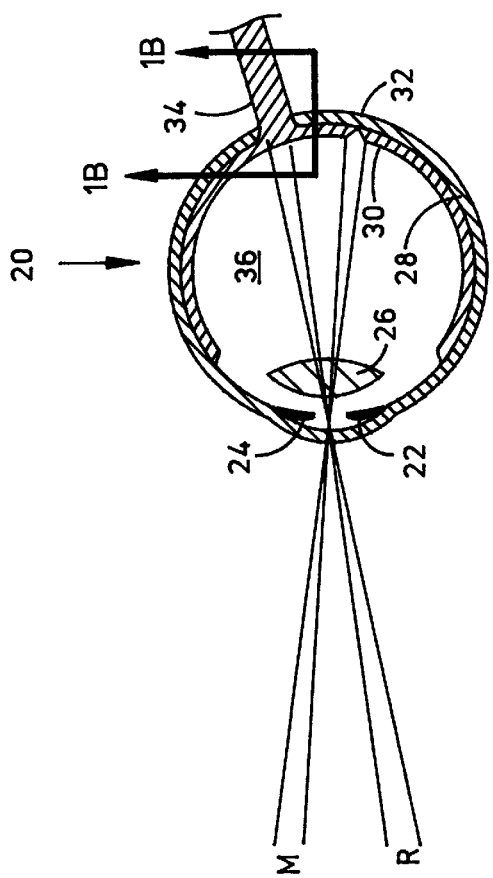
FIG. 1A is a schematic view of the eye identifying various parts of the anterior segment and illustrating two exemplary scan beam paths in the eye.

FIGS. 1A–1B illustrate the human eye 20. A ray of light 21 incident on eye 20 enters through the transparent cornea 22, passes through the pupil 24, traverses the transparent crystalline lens 26, proceeds toward the fundus 28, which is the inside aspect of the back of the eye, and strikes the retina 30 (FIG. 1B), which lines the inner surface of the back of the eye. A central depression in retina 30 identifies the fovea 32, which is the area of the most acute vision and is illuminated by light arriving in the scan region M shown. Retinal nerve fibers arising from all parts of retina 30 travel along the surface of retina 30 and converge to form the optic nerve 34, which is illuminated by light arriving in the scan region R shown. The interior 36 of eye 20 is filled with vitreous humor. Retina 30 (FIG. 1B) is composed of many layers or structures, including, in the area of fundus 28, the internal limiting membrane (ILM) 38, the retinal nerve fiber layer (RNFL) 40, the receptor system 42, the retinal pigment epithelium 44, and the choroid 46. The Henle fiber layer (not shown) is generally located at the level of RNFL 40 in the macula centered at fovea 32. All structures forward of ILM 38 are considered part of the anterior segment of eye 20 and may also be loosely referenced as the "cornea" for purposes of this disclosure because of the corneal dominance of anterior segment birefringence. A portion 45 of light ray 21 is reflected from ILM 38 and the remainder 47 scatters from deeper layers substantially as illustrated in FIG. 1B.

Figure 2:
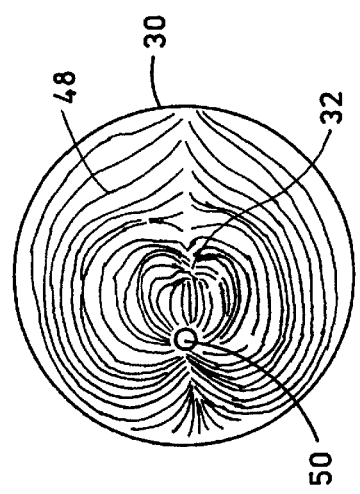
FIG. 2 is a plan view of the posterior retina of a human eye illustrating the characteristic array of retinal nerve fibers.

FIG. 2 is a flat view of the posterior aspect of retina 30, showing the characteristic array of the retinal nerve fibers 48 arising from all parts of retina 30 and converging to the optic papilla or nerve head 50. A large fraction of the retinal nerve fibers arise from the foveal area where the concentration of neural elements is greatest and vision is most acute. As the retinal nerve fibers leave the foveal area, they first travel in a radial direction away from fovea 32, then curve around as necessary to eventually reach optic nerve head 50. This radial pattern of the Henle fiber layer centered at fovea 32 is useful for the method of this invention as discussed below.

Figure 3:
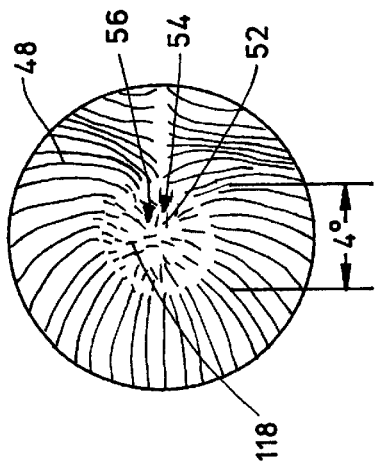
FIG. 3 is a plan view of the foveal area of a human eye illustrating the characteristic array of Henle fibers radiating from the center of the fovea.

FIG. 3 is an enlarged view of the macula centered on fovea 32, showing in greater detail the paths of the nerve fibers leaving fovea 32. The cell bodies 52 of the photoreceptor elements are in the very center of fovea 32. Cell bodies 52 send the axons called Henle fibers 54 to communicate with a ring of ganglion cells 56 surrounding fovea 32. Ganglion cells 56 in turn give rise to long axons of their own, constituting the retinal nerve fibers 48 that travel to optic nerve 34. Henle fibers 54 radiating from photoreceptor cell bodies 52 arranged precisely radially about the center of fovea 32. This precise radial array of Henle fibers 54, ending at the ring of ganglion cells 56, has an overall diameter subtending about four degrees of visual angle. Except for Henle fibers 54 in fovea 32, the only other retinal region having a radial array of nerve fibers is the area around the optic nerve head 50. Optic nerve head 50 subtends a visual angle of about five degrees. Both the Henle fibers and the other retinal-nerve fibers are birefringent, with the slow optic axis ($\theta+\pi/2$) of the birefringence being parallel to the direction of the fiber.

Figure 4:
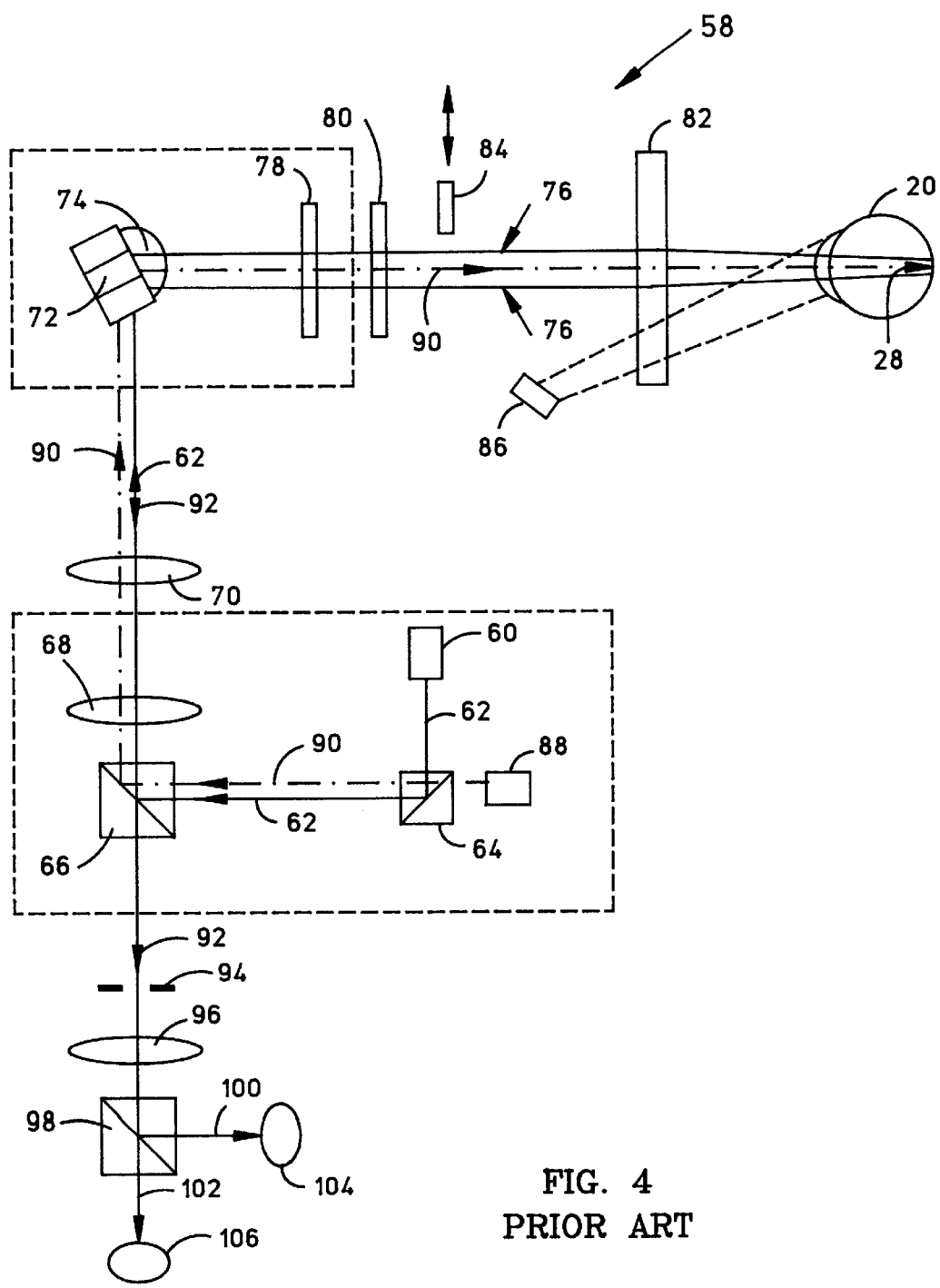
FIG. 4 is a functional block diagram illustrating an exemplary embodiment of a polarimeter apparatus suitable for use with the system of this invention.

FIG. 4 is a functional block diagram illustrating an exemplary embodiment 58 of a polarimeter suitable for use in the ophthalmological system of this invention. Polarimeter 58 is adapted to produce a plurality of pixels $\{S(\delta_T, \theta_T)\}$ representing a two-dimensional polarimetric image suitable for use in analyzing a structure in eye 20 to provide, for example, an image map of the thickness of RNFL 40 or a polarimetric image of the retardance magnitude $\delta_H$ and orientation $\theta_H$ the Henle fiber layer 54. In FIG. 4, a laser diode 60 produces a linearly-polarized diagnostic optical signal 62, which is redirected by the polarizing beam splitter 64 to a non-polarizing beam splitter 66 and therefrom though the collimating lens 68 and the focusing lens 70 along an optical beam axis to the polygon scanner 72 and the galvo-mirror scanner 74. Scanners 72 and 74 provide a two-dimensional beam scan 76, each individual pixel of which has a linear polarization that is rotated by the half-wave plate 78 and the retarder 80, which may be embodied as a VCC or liquid crystal variable retarder (LCVR) or a fixed retarder or any useful combination of one or more thereof. An output lens 82 steers the elements of two-dimensional beam scan 76 to the fundus 28 of eye 20. A moveable calibration test target 84 is used in cooperation with a CCD camera 86 and a fixation laser diode 88 (providing an optical fixation signal 90 that is transmitted along the optical beam axis) to automatically calibrate and orient the various elements of polarimeter 58 to eye 20. A reflected optical diagnostic signal 92 is returned from fundus 28 along the same optical path, to non-polarizing beam splitter 66, from whence it is transmitted through the pinhole 94 and the focusing lens 96 to the polarizing beam splitter 98. Polarizing beam splitter 98 separates the orthogonal polarization components 100 and 102, directing them respectively to the optical detectors 104 and 106. Operation of polarimeter 58 may be readily appreciated with reference to the above discussion the above-cited SLP patents included herein by reference. Not shown is the motor means required for independently rotating half-wave plate 78 about optical beam axis 90 to obtain the second polarimetric images required in accordance with this invention.

Figure 5:
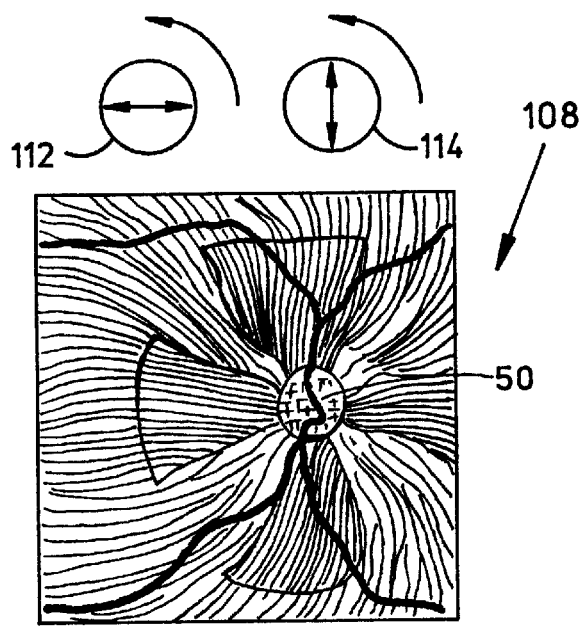
FIG. 5 illustrates a polarimetric image of the RNFL under illumination with a linearly-polarized optical diagnostic signal as detected with a crossed analyzer, corneal birefringence having been eliminated.
Figure 6:
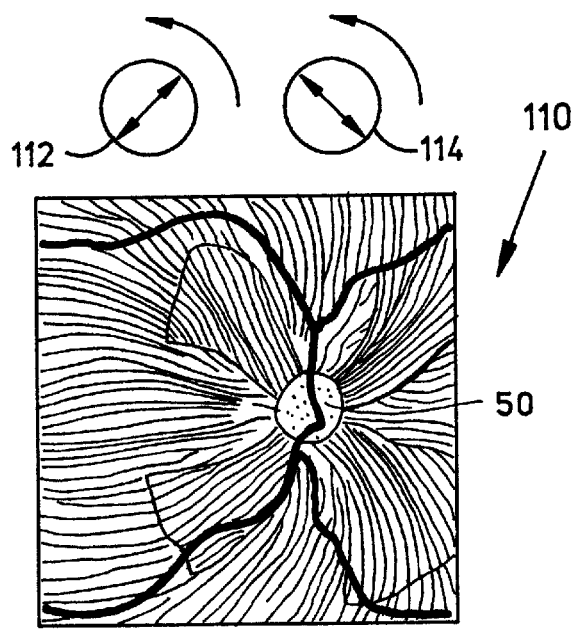
FIG. 6 is identical to FIG. 5, but illustrating a polarimetric image with the linearly-polarized optical diagnostic signal and the analyzer both rotated about 45 degrees.

FIGS. 5 and 6 illustrate the appearance of unprocessed polarimetric images such as those that may be obtained by polarimeter 58 with a VCC disposed to cancel corneal retardance. Polarimetric images 108 and 110 also show some of the same retinal anatomy discussed above in conjunction with FIGS. 2–3. RNFL 40 includes an array of radially arranged nerve fibers 48 that converge to form nerve head 50. Radially arranged nerve fibers 48 are about half the diameter of the wavelength of visible light and act as a linear birefringent medium because of the local parallelism and fractional-wavelength spacing of the fibers. The orthogonal linear polarization orientations 112 and 114 are indicated respectively for the incident diagnostic beam (112) and the analyzer filter (114) for both images 108 and 110. Image 108 exhibits a "cross" pattern of brightness, indicated at 116. The darkness is aligned with incident diagnostic beam and analyzer filter polarization axes 112 and 114. The bright arms correspond to RNFL areas whose radial fiber orientations are rotated 45 degrees to either side of polarization axes 112 and 114. Similarly in FIG. 6, image 110 rotation of incident diagnostic beam axis 112 and analyzer filter axis 114 darkens the areas of similar fiber alignment and brightens the areas with 45-degree misalignment. The image intensity profile taken along an annular path centered at nerve head 50 appears as a modulated wave moving between two extreme values and having a mean value, all of which result from the radial symmetry of the fibers and the birefringence of the various system elements in the measurement path, including fibers 40, cornea 22, and the SLP elements shown in FIG. 4. The radial symmetry and fiber uniformity at the Henle fiber layer in fovea 32 is more predictable than at nerve head 50. The relationship to the optical path elements of the resulting polarimetric image may be described using Mueller matrix notation.

Because the Mueller matrix M is a linear transform, the Mueller matrix for a series of birefringent segments may be expressed as the ordered product of the Mueller matrices for each of the birefringent segments. Consider a SLP measurement beam of polarization state $S_G$ that propagates through the SLP system to the bottom of the retina and returns as a signal of polarization state $S_A = M_T S_G$. Assuming linearity in the system, the total (net) retardance encountered by the SLP measurement beam can be said to be equivalent to a linear retarder having a Mueller matrix $M_T(\delta_T, \theta_T)$, which can be expressed as the ordered product of the Mueller matrices for each of the traversed SLP and biological elements (FIG. 4). The measurement beam (e.g., beam 76) travels through the corneal compensator (e.g. retarder 80), $M_F(\delta_F, \theta_F)$, and the cornea (e.g., cornea 22), $M_C(\delta_C, \theta_C)$, to RNFL 40, through which it passes before it is reflected from a surface, $M(0,0)$, and returns to complete two passes through RNFL 40 (see Eqn. 5), $M_{2N}(2\delta_N, \theta_N)$, before returning back through the anterior segments including cornea 22, $M_C(\delta_C, \theta_C)$, and the corneal compensator, $M_F(\delta_F, \theta_F)$, so that:

$$M_T(\delta_T, \theta_T) = M_F(\delta_F, \theta_F) M_C(\delta_C, \theta_C) M_{2N}(2\delta_N, \theta_N) M_C(\delta_C, \theta_C) M_F(\delta_F, \theta_F) \quad \text{[Eqn. 6]}$$

Eqn. 6 demonstrates that any one of the birefringent components in the measurement path can be determined if the others are known. For example, the Mueller matrix $M_{2N}$ for the RNFL is related to the net measurement beam matrix $M_T$ by $$M_{2N} = (M_F M_C)^{-1} M_T (M_C M_F)^{-1} \quad \text{[Eqn. 7]}$$

where the negative superscript signifies matrix inversion. Clearly, from Eqns. 3 and 7, if the complex retardance ($\delta$, $\theta$)

is known for the corneal compensator and the cornea combination, the net retardance of the measurement signal is sufficient to permit computation of the retardance of the RNFL. Ideally, the corneal compensator exactly cancels the corneal birefringence so that $M_F=(M_C)^{-1}$ and $M_{2N}=M_T$. Similarly, if $M_T$, $M_{2N}$, and $M_F$ are known, then the corneal retardance $\delta_C$ and fast-axis angle $\theta_C$ may be computed from $M_C$. When no corneal compensator is employed, $M_F=(M_F)^{-1}=I$ (the unity diagonal matrix). If sufficient confocal precision is available to isolate the measurement signal backscattered off of an inner surface of the retina, such as a blood vessel surface or ILM 38 (FIG. 1B), then no RNFL retardance is introduced to the measurement signal and $M_{2N}=(M_{2N})^{-1}=I$ in Eqn. 6, so that $$M_T(\delta_T, \theta_T) = I\, M_C\, I\, M_C\, I = M_{2C}(2\delta_C, \theta_C) \quad [\text{Eqn. 8}]$$

Eqn. 8 represents a direct method for measuring corneal retardance $\delta_C=\delta_T/2$ and fast-axis angle $\theta_C=\theta_T$ at a single point in the cornea using a single pair of measurement samples instead of the sixteen samples normally required to populate the entire Mueller matrix. With this corneal retardance $\delta_C$ and fast-axis angle $\theta_C$, Eqn. 7 determines RNFL retardance $(\delta_N, \theta_N)$ (and thus thickness) directly from the retardance $(\delta_T, \theta_T)$ of a second measurement signal reflected from the rear of the retina. However, available SLP methods do not provide the precision needed to distinguish a focal plane at ILM 38 from one at the rear of the retina. Available depth resolution is comparable to the entire retinal thickness for most locations. Depth resolution much less than retinal thickness is needed to isolate the optical measurement signal ILM reflections from those off of the deeper retinal structures. Moreover, SLP systems employing linear polarization state generator ($PS_G$) and analyzer (PSA) components cannot distinguish between fast-axis and slow-axis orientation, leaving an extra unknown variable in Eqn. 6.

As described in the above-cited SLP U.S. Pat. No. 6,356,036 B1, the anterior segment birefringence $(\delta_C, \theta_C)$ may be determined from measurement of an annular retardance magnitude $\delta_T$ profile of the Henle fiber layer such as, for example, a 3-degree annulus (not shown) centered within fovea 32 in the macula (FIG. 3).

The orientation axis $\theta_C$ of the anterior segment birefringence is computed from the measured macular retardance magnitude $\delta_T$ profile by relying on the radial geometry of the Henle fiber layer wherein the slow-axis $(\theta_H+\pi/2)$ is known to be aligned with the radial fibers radiating symmetrically from the fovea. According to Eqn. 4, the combined retardance $\delta_T$ of two retarders varies with the angle between the fast-axes $(\theta_C-\theta_H)$ of the two retarders. At the macular locus where the slow-axis $(\theta_H+\pi/2)$ of the Henle fiber layer is parallel to the slow-axis $(\theta_C+\pi/2)$ of the anterior segment, the combined retardance is the sum of the two $(\delta_T=\delta_C+\delta_H)$, which shows up as a maximum in the macular retardance profile. At the macular locus where the slow-axis $(\theta_H+\pi/2)$ of the Henle fiber layer is perpendicular to the slow-axis $(\theta_C+\pi/2)$ of the anterior segment, the combined retardance is the difference of the two $(\delta_T=\delta_C-\delta_H)$, which shows up as a minimum in the macular retardance profile. The two maxima are located by performing a least-squares fit over the annular retardance profile with Eqn. 4 so that a line connecting the two maxima in the annular macular profile indicates the slow-axis orientation $(\theta_C+\pi/2)$ of the anterior segment retardance.

The magnitude $\delta_C$ of the anterior segment retardance is also computed from the annular macular profile. The shape of the annular macular profile depends on the relative magnitudes of the anterior segment retardance $\delta_C$ and the Henle fiber layer retardance $\delta_H$. The three possible cases are $(\delta_C<\delta_H)$, $(\delta_C=\delta_H)$, and $(\delta_C>\delta_H)$, where the anterior segment retardance $\delta_C$ is less than, equal to, or greater than the Henle fiber layer retardance $\delta_H$, respectively. Because of the radial symmetry of the Henle fiber layer, each of these three cases is evidenced by a modulation of the annular macular profile amplitude, which may be described in terms of mean and peak-to-peak (maximum-minimum) amplitudes. When the anterior segment retardance is higher than that of the Henle fiber layer $(\delta_C>\delta_H)$, the mean retardance amplitude of the annular macular profile is dominated by the anterior segment. When the retardance of the anterior segment is less than that of the Henle fiber layer $(\delta_C<\delta_H)$, half of the peak-to-peak amplitude of the annular macular profile is exactly equal to the anterior segment retardance $\delta_C$. Two retardance magnitudes $\delta_1$ and $\delta_2$ can be determined by performing a least-squares fit to the annular macular retardance profile using Eqn. 4. These two values are then allocated to $\delta_C$ and $\delta_H$ by applying a set of rules based on the macular profile characteristics, thereby obtaining the anterior segment retardance magnitude $\delta_C$. Generally, the variation of corneal retardance over the small (2 mm) SLP scanning region is quite small and a fixed value may be safely assumed.

When the VCC is embodied as two identical rotatable retarders (e.g., retarders 78 and 80 in FIG. 4), the magnitude $\delta_F$ is set by varying the angle between the fast-axes of the two identical retarders. The fast axis $\theta_F$ of the VCC is set by rotating both retarders together so that $\theta_F$ is orthogonal to $\theta_C$. Although a VCC consisting of two fixed retarders is a retarder plus a rotator, in the double-pass SLP setup, the rotation in the diagnostic signal 62 (illuminating beam) is canceled by the rotation in the reflected diagnostic signal 92 (reflected beam), and the combination functions as a simple retarder. By Eqn. 7, once the VCC retardance $(\delta_F, \theta_F)$ is correctly adjusted so that $M_F M_C=I$, the total retardance $(\delta_T, \theta_T)$ measured with the SLP is equal to twice the RNFL retardance $(2\delta_N, \theta_N)$ or the Henle fiber layer retardance $(2\delta_H, \theta_H)$, depending on scan locale.

Accordingly, a properly-compensated SLP image of the macula shows a radially-symmetric uniform pattern characteristic of the Henle fiber layer (assuming no macular pathology) and a properly-compensated SLP image of the peripapillary RNFL shows a pattern consistent with the actual anatomy of the eye under test (e.g., FIGS. 5–6), which is the ultimate objective. VCC effectiveness may be confirmed by examining the radial symmetry of the compensated macular image. If the anterior segment compensation is complete, the combined retardance of the VCC and the anterior segment is zero $(M_F M_C=I)$, so that the macular image is uniform and dark around the fovea and exhibits a flat (unmodulated) annular retardance profile. Incomplete compensation is exhibited as a residual modulation in the annular retardance profile, which can be measured using the anterior segment determination method described above. But this technique alone does nothing to eliminate the fast-or-slow ambiguity in the retardance orientation image. Without a new procedure, an additional retinal scan with the VCC set to another orientation is needed to eliminate this ambiguity by adding the independent sample required to solve Eqn. 6. Suitable new procedures are now described.

One embodiment of the system of this invention provides a post-measurement analytical method for eliminating the fast-or-slow orientation axis ambiguity from a single RNFL polarimetric image before processing to remove the effects of anterior birefringence. The method exploits the unexpectedly advantageous observation that measured retardance magnitude $\delta_T$ and fast-axis orientation $\theta_T$ can be determined from a single scan image provided that it includes a region where the biological tissue properties are known to fix the retardance slow-axis orientation $(\theta_T + \pi/2)$. If a single ("seed") pixel in an RNFL scan image is associated with a known slow-axis orientation $(\theta_N + \pi/2)$, the orientation axis measured for that pixel can be resolved as either fast or slow, depending on the biological tissue orientation. Because the retardance orientation distribution over the scan image is generally continuous, without discontinuities of over 45° between adjacent image pixels, the fast-or-slow ambiguity can be resolved for the remainder of the scan image orientation axes based on such a seed pixel. For example, a seed pixel may be selected at the point 118 in fovea 32 (FIG. 3), which is well-behaved and most likely to show alignment of the slow-axis with the biological Henle fiber orientation.

Starting from a seed pixel, the orientation values for the entire image can be resolved according to the method of this invention. This method may be used either with or without any suitable anterior segment compensation scheme to permit RNFL measurement in a single scan image. External retardance bias $(\delta_F, \theta_F)$ should be added to ensure that the measured retardance values are large enough to ensure validity of the axis continuity assumption over the entire image. A VCC may be used to provide this bias, for example, or any other suitable optical component with a known retardance, such as a fixed retarder or a liquid crystal, or a combination of components. Preferably, a variable retarder is used as the bias retarder (either rotationally adjustable, or magnitude adjustable, or both) to bias the measurement data. A fixed bias retarder can be used when the range of retinal retardance is relatively small and the corneal birefringence axis and magnitude distributions are known. By introducing a relatively large retardation bias compared to retinal retardance, the measured axis is similar for neighboring image pixels and the axis ambiguity can be removed in the manner discussed. Accordingly, a single image measurement is sufficient to determine both corneal birefringence and retinal birefringence. However, while introducing sufficient bias retardance to ensure a smooth axis image, the total single-pass retardance of the measurement beam, including the bias retarder and the eye should not exceed $\pi/2$. Blood vessels and noise may also be removed from the orientation axis image with any useful image processing method to eliminate discontinuities before resolving ambiguity from the seed pixel throughout the axis image.

Figure 7:
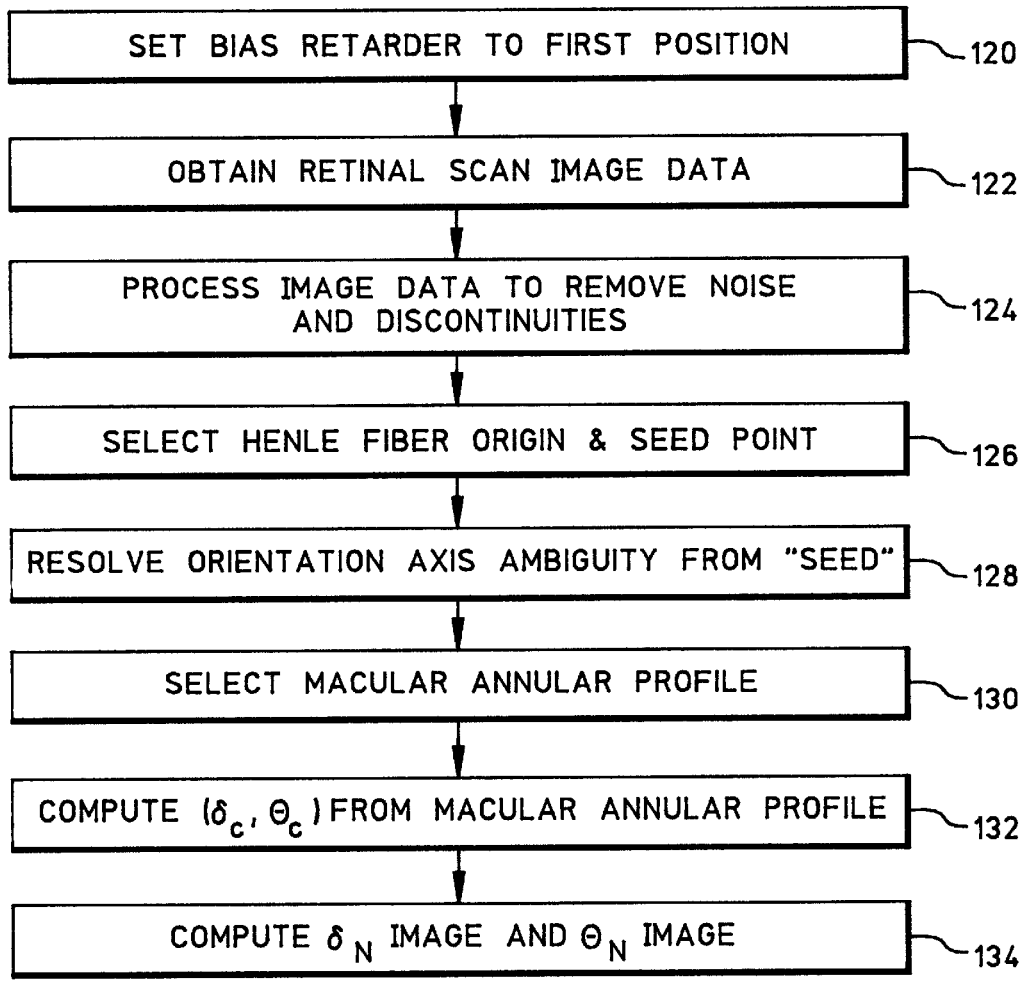
FIG. 7 is a block diagram illustrating a flow chart of the method of this invention for single-scan polarimetry without variable corneal compensation (VCC)

FIG. 7 is a block diagram of a flow chart illustrating the method of this invention for single-scan polarimetry without using a VCC. In the first step 120, a bias retarder $M_H$ (e.g., retarder 78 and/or 80 in FIG. 4) is set to a first position to provide sufficient bias to ensure continuity of orientation angles in the polarimetric image and a retinal polarimetric scan image is acquired and stored in the next step 122. The bias retarder can also serve to improve measurement accuracy and reproducibility, by shifting the total retardance away from the two extremes (low values of RNFL retardance alone and high values close to quarter wavelength), which are more susceptible to system noise from detectors and analog-to-digital conversion circuits and the like. In step 124, the stored image is processed to remove blood vessels and noise and any other discontinuities from the stored polarimetric image, which includes measured retardance magnitude $\delta_T$ and a measured orientation angle $\theta_T$ for each pixel. However, because the fast or slow axis identity of the orientation angles $\{\theta_T\}$ is unknown, each measured angle $\theta_T$ could be either the fast axis or the slow axis. In step 126, the seed point is selected, preferably in the Henle fiber layer at the macula (e.g., pixel 118 in FIG. 3) and the fast axis of measured angle $\theta_{TS}$ is identified by observing the fiber orientation and recognizing that the slow axis is most likely aligned with the biological fiber. The fast axis is then recognized as orthogonal to the slow axis. If the measured angle $\theta_{TS}$ is nearly aligned with the fiber, it is corrected by adding $\pi/2$ to value the fast axis for the seed pixel as $(\theta_{TS} + \pi/2)$. If the measured angle $\theta_{TS}$ is nearly orthogonal to the fiber, it is not corrected and the fast axis for the seed pixel is valued as $\theta_{TS}$. In the next step 128, the fast axes of the remaining pixels are identified based on (a) the knowledge of the seed pixel fast axis and (b) recognition that the adjacent pixel orientation angles cannot vary by more than $\pi/4$. All of the pixel orientation angles $\{\theta_T\}$ can be quickly resolved one by one to produce a stored polarimetric image of the retina without orientation angle ambiguity. In the step 130, an annular macular profile is selected from the resolved image of the fovea and the anterior segment retardance $(\delta_C, \theta_C)$ is computed in step 132 from the mean value and peak-to-peak value of the annular modulation in the manner discussed above. Finally, in the step 134, the desired RNFL polarimetric image $\{S(\delta_N, \theta_N)\}$ is computed pixel by pixel from the resolved polarimetric image $\{S(\delta_T, \theta_T)\}$ using Eqn. 7.

An alternative embodiment of the system of this invention provides a post-measurement analytical method for directly computing the anterior segment retardance $(\delta_C, \theta_C)$ and the RNFL retardance from the RNFL polarimetric image by using a plurality of the image pixels to perform a least-squares fit to solve for $\delta_C$, $\theta_C$, $\delta_N$ and $\theta_N$ in accordance with Eqns. 9A–B, where $M_{F1}$ and $M_{F2}$ represent a fixed bias retarder in two different positions:

$$M_{T1}(\delta_{T1}, \theta_{T1}) = M_{F1}(\delta_F, \theta_{F1}) M_C(\delta_C, \theta_C) M_{2N}(2\delta_N, \theta_N) M_C(\delta_C, \theta_C) M_{F1}(\delta_F, \theta_{F1}) \quad \text{[Eqn. 9A]}$$

$$M_{T2}(\delta_{T2}, \theta_{T2}) = M_{F2}(\delta_F, \theta_{F2}) M_C(\delta_C, \theta_C) M_{2N}(2\delta_N, \theta_N) M_C(\delta_C, \theta_C) M_{F2}(\delta_F, \theta_{F2}) \quad \text{[Eqn. 9B]}$$

Data from a macular scan image of the Henle fiber layer may also be used to solve for $\delta_C$, $\theta_C$, $\delta_H$ with $(\theta_H + \pi/2)$ assumed to be radially-oriented by a least-squares fit to Eqns. 10A–B.

$$M_{T1}(\delta_{T1}, \theta_{T1}) = M_{F1}(\delta_F, \theta_{F1}) M_C(\delta_C, \theta_C) M_{2H}(2\delta_H, \theta_H) M_C(\delta_C, \theta_C) M_{F1}(\delta_F, \theta_{F1}) \quad \text{[Eqn. 10A]}$$

$$M_{T2}(\delta_{T2}, \theta_{T2}) = M_{F2}(\delta_F, \theta_{F2}) M_C(\delta_C, \theta_C) M_{2H}(2\delta_H, \theta_H) M_C(\delta_C, \theta_C) M_{F2}(\delta_F, \theta_{F2}) \quad \text{[Eqn. 10B]}$$

The inventors have performed simulations to quantify the advantages of this embodiment of the system of this invention. The anterior segment retardance magnitude $\delta_C$ and orientation $\theta_C$ and the Henle fiber layer retardance magnitude $\delta_H$ can all be well determined from the macula image data taken with the bias retarder set in two positions (Eqns. 10). The goodness of fit for $\delta_C$ and $\theta_C$ is unaffected by the $\theta_C$ value but depends on the $\delta_C$ value, which must not be too low. For low values of $\delta_C$, the fit can be improved by including more pixels in the fitting. Radial Henle fiber retardance orientation $\theta_H$ and uniform retardance magnitude $\delta_H$ is assumed.

The anterior segment retardance magnitude $\delta_C$ and orientation $\theta_C$ and the RNFL retardance magnitude $\delta_N$ and orientation $\theta_N$ can all be well determined from the peripapillary RNFL image data taken with the bias retarder set in two positions (Eqns. 9). The goodness of fit for $\delta_C$ and $\theta_C$ strongly depends on the RNFL orientation $\theta_N$ boundaries (uncertainty) in the least squares fit. At lower values of RNFL retardance magnitude $\delta_N$, the $\delta_C$ and $\theta_C$ values are well estimated and insensitive to the RNFL orientation $\theta_N$ boundaries (uncertainty). But the $\delta_C$ and $\theta_C$ fit is very sensitive to the RNFL orientation $\theta_N$ boundaries at higher values of RNFL retardance magnitude $\delta_N$ and can be well determined only when $\theta_N$ can be estimated from biological fiber orientation to within one or two degrees. Except for low values of $\delta_N$, the fit can be improved by including more pixels in the fitting. Two or three pixels are generally sufficient but six or seven pixels can improve accuracy. The goodness of fit also depends on the $\delta_C$ value and strong corneal retardance can provide better estimation. Corneal retardance orientation $\theta_C$ values that vary too much from the presumed value can degrade the fit. This embodiment of the system of this invention requires selection of four or more image pixels having low RNFL retardance magnitude $\delta_N$ and well-defined orientation $\theta_N$. Such pixels may easily be selected from the RNFL image.

Either of these two least-squares fitting methods (Eqns. 9–10) yields measured values for anterior segment retardance ($\delta_C$, $\theta_C$) suitable for use with Eqn. 7 to compute the retardance magnitude $\delta_N$ image and the retardance orientation $\theta_N$ image from the original RNFL image, thereby achieving the objective of the measurements without using corneal compensation. The RNFL method (Eqns. 9) may fail in extreme situations, in which case the macular method (Eqns. 10) may be used instead to obtain anterior segment retardance ($\delta_C$, $\theta_C$) before processing the RNFL image to obtain RNFL retardance ($\delta_N$, $\theta_N$). The RNFL method is preferred because it simplifies the operational procedure and eliminates any possible systematic error in the corneal and RNFL orientation axes because both axes are derived from the same data. Both methods require accurate expectation for the macula and the RNFL orientation axes, respectively, which requires designation of the "origin" of the radiating neural patterns in the image (fovea or optic disk, respectively) before processing.

Figure 8:
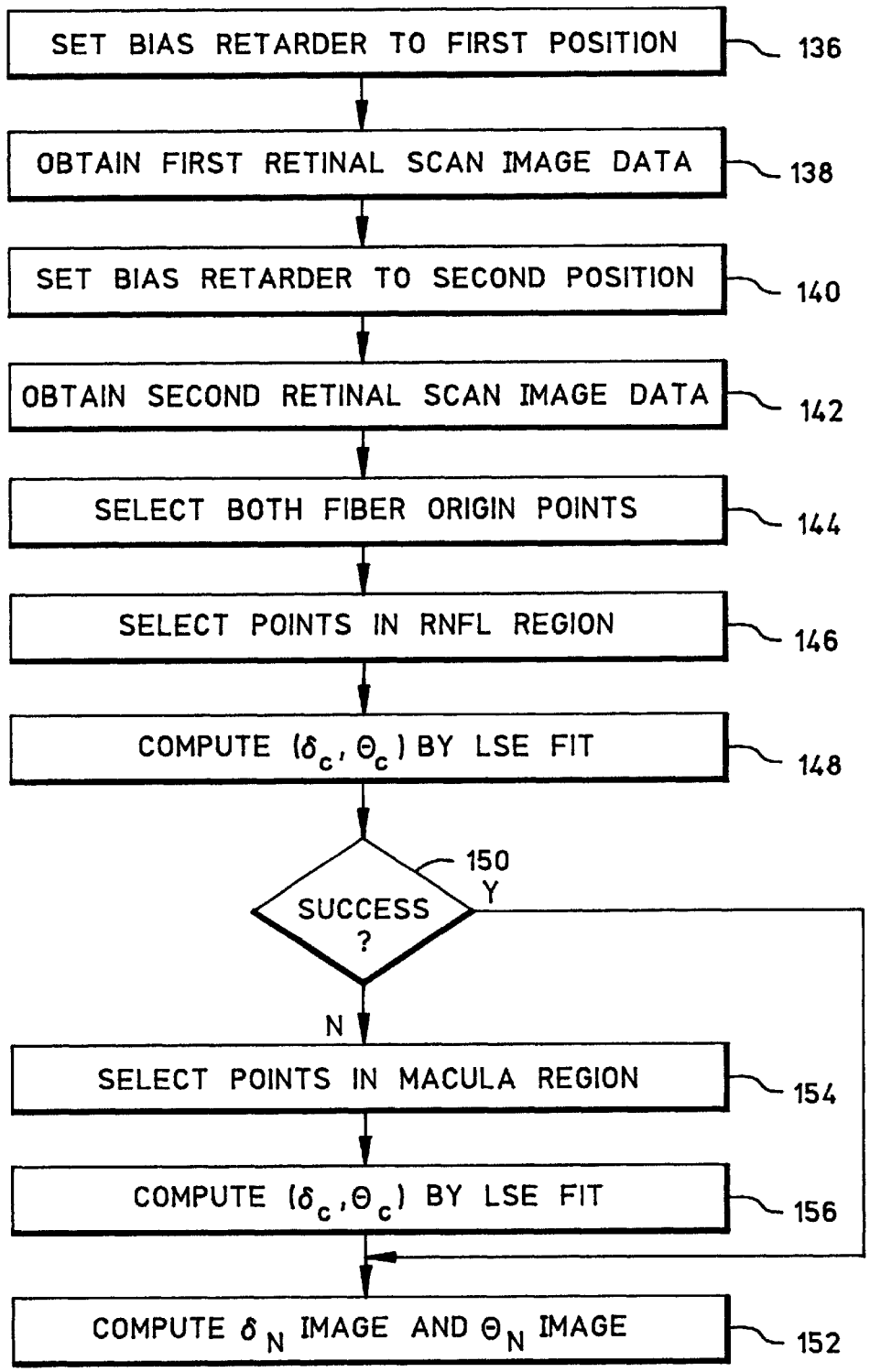
FIG. 8 is a block diagram illustrating a flow chart of the method of this invention for RNFL polarimetry without VCC.

FIG. 8 is a block diagram of a flow chart illustrating the alternative method of this invention for RNFL polarimetry without VCC. In the first step 136, a bias retarder $M_H$ (e.g., retarder 78 or 80 in FIG. 4) is set to a first position to provide sufficient bias to ensure that the later processing steps will converge successfully and a first polarimetric image is scanned and stored in the step 138. The bias retarder is adjusted in step 140 and a second polarimetric image is scanned and stored in the step 142. In the next step 144, the two radial fiber origins are identified in the images to permit selection of pixels from regions with well-ordered retardance distributions. In the step 146, four pixels are selected in the RNFL region near nerve head 50 (FIG. 2), although any plurality up to seven or more is useful. In step 148, the four sets of pixel data are fitted to minimize least-square errors according to Eqns. 9A–B, thereby computing the anterior segment retardance ($\delta_C$, $\theta_C$) The RNFL retardances $\{\delta_N, \theta_N\}$ are also provided by the fitting procedure for the selected points and the success of the fit may depend on a close estimation of the orientation values $\{\theta_N\}$ based on fiber distribution and geometry. In step 150, the fit is evaluated for success, which is expected for a well-distributed RNFL, and the desired RNFL polarimetric image $\{S(\delta_N, \theta_N)\}$ is computed pixel by pixel from the stored images $\{S(\delta_T, \theta_T)\}$ using Eqn. 7 in the final step 152. If step 150 fails, the steps 154 and 156 perform a least-square error minimizing fit to Eqns. 10A–B of the data for several pixels in the macular region using the Henle fiber layer, which may be more regular than the RNFL (such as in cases of RNFL pathology).

Figure 9:
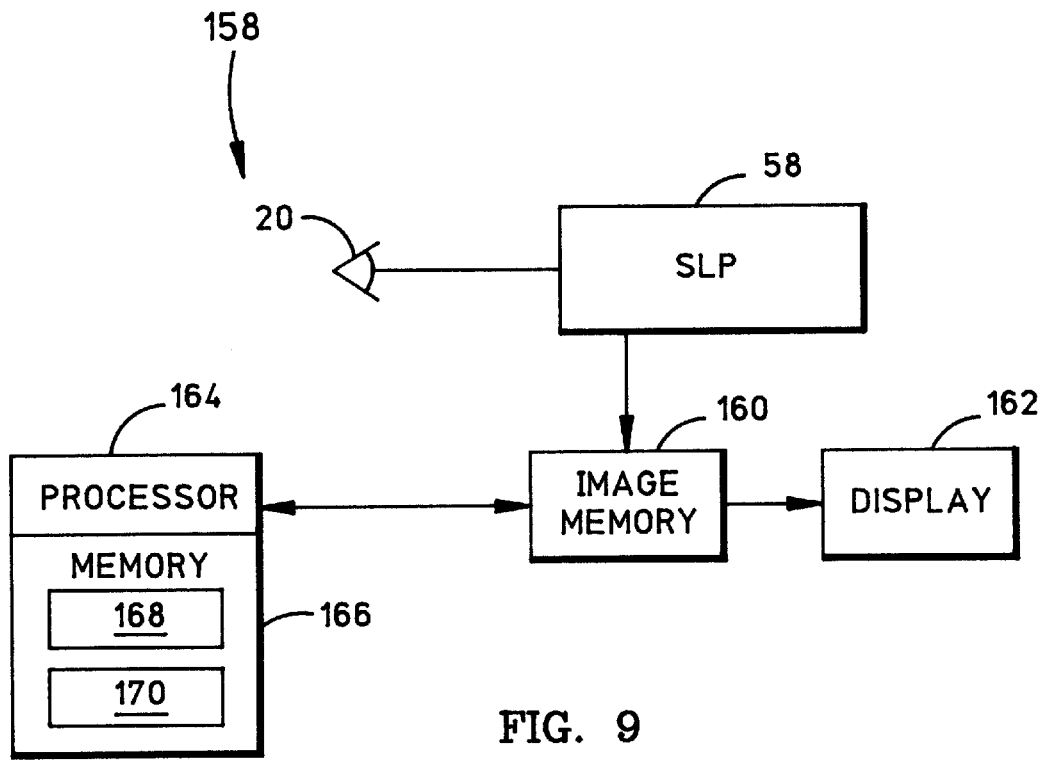
FIG. 9 is a functional block diagram illustrating the system of this invention.

FIG. 9 is a functional block diagram of an exemplary embodiment 158 of the ophthalmological system of this invention. Polarimeter 58 is coupled to the image memory 160, which in turn is coupled to a display 162 for viewing images stored in memory 160. Memory 160, display 162 and polarimeter 58 are all under the control of the processor 164, which includes a program memory 166 adapted to store executable program instructions. These program instructions may be organized as modules, exemplified by the modules 168 and 170, which may, for example, include program means for removing noise and discontinuities from polarimetric images or program means for selecting a seed pixel $S(\delta_{TS}, \theta_{TS})$ corresponding to a biological feature of the retinal structure in a polarimetric image. Modules 168 and 170 may also, for example, include means for selecting the fast axis of the seed pixel retardance angle $\theta_{TS}$ corresponding to the associated biological tissue properties or processing means for propagating the fast-axis identification through the entire image. Without limitation, modules 168 and 170 may include processing instructions for performing least-square error (LSE) calculations to fit pixel data to selected equations or equation solving means for computing a RNFL image from a measured image by solving a Mueller matrix equation such as Eqns. 6 and 7. Based on these teachings, the details of all such program modules are within the state of the software arts and may be implemented by a skilled practitioner without undue experimentation.

Figure 10:
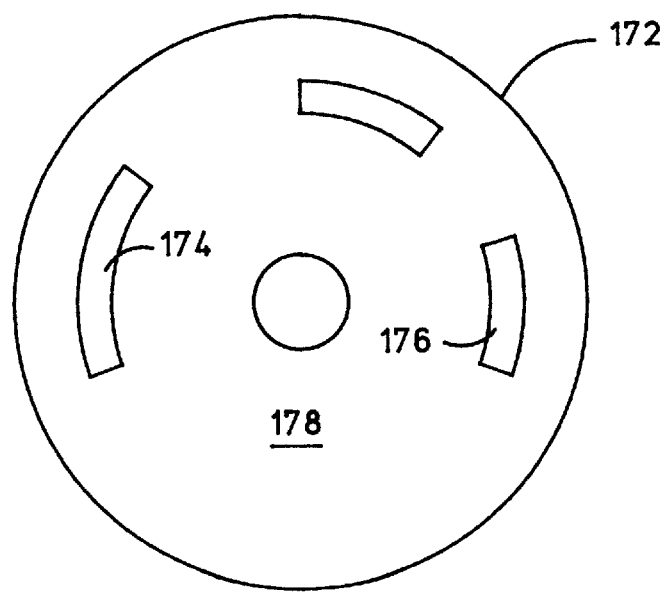
FIG. 10 is a schematic view of an exemplary computer program product (CPP) embodiment in accordance with this invention.

FIG. 10 is a schematic view of an exemplary computer program product (CPP) embodiment 172 in accordance with this invention. CPP 172 includes a plurality of computer program modules exemplified by the modules 174 and 176 recorded on the CDROM medium 178 for use in directing a computer to perform specific operations. For example, modules 174 and 176 may include program instructions for directing ophthalmological system 158 to determine the fast axes of the pixel retardance angles $\{\theta_T\}$ corresponding to a biological feature of the retinal structure in the first polarimetric image or processing code for directing ophthalmological system 58 to determine anterior segment retardance magnitude $\delta_C$ and orientation $\theta_C$ values corresponding to the variation of the retardance magnitude $\delta_T$ over an annular region of a polarimetric image. Although CPP 172 is illustrated as a CDROM embodiment, any other useful CPP embodiment may be used as well with the system of this invention, such as, for example, a magnetic disk embodiment or a memory stick embodiment.

Clearly, other embodiments and modifications of this invention may occur readily to those of ordinary skill in the art in view of these teachings. Therefore, this invention is to be limited only by the following claims, which include all such embodiments and modifications when viewed in conjunction with the above specification and accompanying drawing.

We claim:

1. A machine-implemented method for analyzing the birefringence of a retinal structure of an eye having an anterior segment and a pupil, the method comprising the steps of (a) producing a first polarimetric image of the retinal structure having a plurality of pixels $\{S(\delta_T, \theta_T)\}$ each representing a measured retardance magnitude $\delta_T$ and orientation angle $\theta_T$;

(b) determining the fast axes of the pixel retardance angles $\{\theta_T\}$ corresponding to a biological feature of the retinal structure in the first polarimetric image;

(c) determining anterior segment retardance magnitude $\delta_C$ and orientation $\theta_C$ values corresponding to the variation of the retardance magnitude $\delta_T$ over an annular region of the first polarimetric image; and (d) computing a second polarimetric image of the retinal structure having a plurality of pixels $\{S(\delta_N, \theta_N)\}$ each corresponding to a first polarimetric image pixel $S(\delta_T, \theta_T)$ from which the effects of the anterior segment retardance are removed.

2. The method of claim 1 further comprising the steps of:

(a.1) producing an optical diagnostic signal having a predetermined polarization state;

(a.2) directing the optical diagnostic signal into the eye through the pupil, such that the optical diagnostic signal is reflected from a selected point on the retinal structure back through the pupil;

(a.3) determining the polarization state of the reflected optical diagnostic signal;

(a.4) producing an electrical analysis signal $S(\delta_T, \theta_T)$ representing the polarization state of the reflected optical diagnostic signal; and (a.5) storing the electrical analysis signal $S(\delta_T, \theta_T)$ as a pixel of the first polarimetric image.

3. The method of claim 2 further comprising the step of:

(a.2.1) directing the optical diagnostic signal through a bias retardance $\delta_F$ having a first orientation $\theta_F$ into the eye through the pupil.

4. The method of claim 3 further comprising the step of:

(d.1) computing the second polarimetric image such that $$M_{2N} = (M_F M_C)^{-1} M_T (M_C M_F)^{-1}.$$

5. The method of claim 1 further comprising the step of:

(b.1) selecting a seed pixel $S(\delta_{TS}, \theta_{TS})$ in the first polarimetric image corresponding to the biological feature of the retinal structure;

(b.2) selecting the fast axis of the seed pixel retardance angle $\theta_{TS}$ corresponding to the associated biological tissue properties; and (b.3) evaluating the fast axes the retardance angles $\{\theta_T\}$ for the first polarimetric image pixels responsive to the seed pixel retardance angle $\theta_{TS}$ fast axis value.

6. The method of claim 5 further comprising the step of:

(b.1.1) removing noise and discontinuities from the first polarimetric image.

7. The method of claim 1 further comprising the step of:

(d.1) computing the second polarimetric image such that $$M_{2N} = (M_C)^{-1} M_T (M_C)^{-1}.$$

8. An ophthalmological system for analyzing the birefringence of a retinal structure of an eye having an anterior segment and a pupil, comprising:

a scanning laser polarimeter for producing a first polarimetric image of the retinal structure having a plurality of pixels $\{S(\delta_T, \theta_T)\}$ each representing a measured retardance magnitude $\delta_T$ and orientation angle $\theta_T$;

first processor means for determining the fast axes of the pixel retardance angles $\{\theta_T\}$ corresponding to a biological feature of the retinal structure in the first polarimetric image;

second processor means for determining the anterior segment retardance magnitude $\delta_C$ and orientation $\theta_C$ values corresponding to the variation of the retardance magnitude $\Delta_T$ over an annular region of the first polarimetric image; and third processor means for computing a second polarimetric image of the retinal structure having a plurality of pixels $\{S(\delta_N, \theta_N)\}$ each corresponding to a first polarimetric image pixel $S(\delta_T, \theta_T)$ from which the effects of the anterior segment retardance are removed.

9. The system of claim 8 further comprising:

generator means for producing an optical diagnostic signal having a predetermined polarization state;

optical means for directing the optical diagnostic signal into the eye through the pupil, such that the optical diagnostic signal is reflected from a selected point on the retinal structure back through the pupil;

analyzer means for determining the polarization state of the reflected optical diagnostic signal;

detector means for producing an electrical analysis signal $S(\delta_T, \theta_T)$ representing the polarization state of the reflected optical diagnostic signal; and memory means for storing the electrical analysis signal $S(\delta_T, \theta_T)$ as a pixel of the first polarimetric image.

10. The system of claim 9 further comprising:

a bias retardance $\delta_F$ having a first orientation $\theta_F$ disposed in the optical diagnostic signal path to the eye.

11. The system of claim 8 further comprising:

selector means for selecting a seed pixel $S(\delta_{TS}, \theta_{TS})$ in the first polarimetric image corresponding to the biological feature of the retinal structure; resolver means for selecting the fast axis of the seed pixel retardance angle $\theta_{TS}$ corresponding to the associated biological tissue properties; and fourth processor means for evaluating the fast axes the retardance angles $\{\theta_T\}$ for the first polarimetric image pixels responsive to the seed pixel retardance angle $\theta_{TS}$ fast axis value.

12. A machine-implemented method for analyzing the birefringence of a retinal structure of an eye having an anterior segment and a pupil, the method comprising the steps of:

(a) producing a first polarimetric image of the retinal structure each having a plurality of pixels $\{S(\delta_{T1}, \theta_{T1})\}$ each representing a measured retardance magnitude $\delta_{T1}$ and orientation angle $\theta_{T1}$;

(b) producing a second polarimetric image of the retinal structure having a plurality of pixels $S(\delta_{T2}, \theta_{T2})$ each representing a measured retardance magnitude $\delta_{T2}$ and orientation angle $\theta_{T2}$;

(c) computing, for a plurality of pixels $\{S_i\}$ from the first and second polarimetric images, the anterior segment retardance magnitude $\delta_C$ and orientation $\theta_C$ values that provide a minimum least-squares error fit of a Mueller equation; and (d) computing a third polarimetric image of the retinal structure having a plurality of pixels $\{S(\delta_N, \theta_N)\}$ each corresponding to a first or second polarimetric image pixel $S(\delta_T, \theta_T)$ from which the effects of the anterior segment retardance are removed.

13. The method of claim 12 further comprising the steps of (a.1) producing an optical diagnostic signal having a predetermined polarization state;

(a.2) directing the optical diagnostic signal through a bias retardance $\delta_F$ having a first orientation $\theta_{F1}$ into the eye through the pupil, such that the optical diagnostic signal is reflected from a selected point on the retinal structure back through the pupil;

(a.3) determining the polarization state of the reflected optical diagnostic signal;

(a.4) producing an electrical analysis signal $S(\delta_{T1}, \theta_{T1})$ representing the polarization state of the reflected optical diagnostic signal;

(a.5) storing the electrical analysis signal $S(\delta_{T1}, \theta_{T1})$ as a pixel of the first polarimetric image;

(b.1) directing the optical diagnostic signal through a bias retardance $\delta_F$ having a second orientation $\theta_{F2}$ into the eye through the pupil, such that the optical diagnostic signal is reflected from a selected point on the retinal structure back through the pupil;

(b.2) producing a second electrical analysis signal $S(\delta_{T2}, \theta_{T2})$ representing the polarization state of the reflected optical diagnostic signal; and (b.3) storing the second electrical analysis signal $S(\delta_{T2}, \theta_{T2})$ as a pixel of the second polarimetric image.

14. The method of claim 12 further comprising the steps of:

(c.1) computing, for a plurality of pixels $\{S_i\}$ from the first and second polarimetric images, the anterior segment retardance magnitude $\delta_C$ and orientation $\theta_C$ values and the retinal structure retardance magnitude $\{\delta_{Ni}\}$ and orientation $\{\theta_{Ni}\}$ values that provide a minimum least-squares error fit of $$M_T(\delta_T, \theta_T) = M_F(\delta_F, \theta_F) M_C(\delta_C, \theta_C) M_{2N}(2\delta_N, \theta_N) M_C(\delta_C, \theta_C) M_F(\delta_F, \theta_F).$$

15. The method of claim 12 further comprising the step of:

(d.1) computing the second polarimetric image such that $$M_{2N} = (M_F M_C)^{-1} M_T (M_C M_F)^{-1}.$$

16. An ophthalmological system for analyzing the birefringence of a retinal structure of an eye having an anterior segment and a pupil, comprising:

a scanning laser polarimeter for producing a first and second polarimetric images of the retinal structure each having a plurality of pixels $\{S(\delta_T, \theta_T)\}$ each representing a measured retardance magnitude $\delta_T$ and orientation angle $\theta_T$;

first processor means for computing, for each of a plurality of pixels $\{S_i\}$ from the first and second polarimetric images, the anterior segment retardance magnitude $\delta_C$ and orientation $\theta_C$ values that provide a minimum least-squares error fit of a Mueller equation; and second processor means for computing a third polarimetric image of the retinal structure having a plurality of pixels $\{S(\delta_N, \theta_N)\}$ each corresponding to a first or second polarimetric image pixel $S(\delta_T, \theta_T)$ from which the effects of the anterior segment retardance are removed.

17. The system of claim 16 further comprising:

generator means for producing an optical diagnostic signal having a predetermined polarization state;

optical means for directing the optical diagnostic signal into the eye through the pupil, such that the optical diagnostic signal is reflected from a selected point on the retinal structure back through the pupil;

analyzer means for determining the polarization state of the reflected optical diagnostic signal;

detector means for producing an electrical analysis signal $S(\delta_T, \theta_T)$ representing the polarization state of the reflected optical diagnostic signal; and memory means for storing the electrical analysis signal $S(\delta_T, \theta_T)$ as a pixel of the first polarimetric image.

18. A computer program product for use in an ophthalmological system for analyzing the birefringence of a retinal structure of an eye having an anterior segment and a pupil, the ophthalmological system including a scanning polarimeter for producing a first polarimetric image of the retinal structure having a plurality of pixels $\{S(\delta_T, \theta_T)\}$ each representing a measured retardance magnitude $\delta_T$ and orientation angle $\theta_T$, the computer program product comprising:

a recording medium;

means recorded on the recording medium for directing the ophthalmological system to determine the fast axes of the pixel retardance angles $\{\theta_T\}$ corresponding to a biological feature of the retinal structure in the first polarimetric image;

means recorded on the recording medium for directing the ophthalmological system to determine anterior segment retardance magnitude $\delta_C$ and orientation $\theta_C$ values corresponding to the variation of the retardance magnitude $\delta_T$ over an annular region of the first polarimetric image; and means recorded on the recording medium for directing the ophthalmological system to compute a second polarimetric image of the retinal structure having a plurality of pixels $\{S(\delta_N, \theta_N)\}$ each corresponding to a first polarimetric image pixel $S(\delta_T, \theta_T)$ from which the effects of the anterior segment retardance are removed.

19. A computer program product for use in an ophthalmological system for analyzing the birefringence of a retinal structure of an eye having an anterior segment and a pupil, the ophthalmological system including a scanning polarimeter for producing first and second polarimetric images of the retinal structure each having a plurality of pixels $S(\delta_T, \theta_T)$ each representing a measured retardance magnitude $\delta_T$ and orientation angle $\theta_T$, the computer program product comprising:

a recording medium;

means recorded on the recording medium for directing the ophthalmological system to compute, for a plurality of pixels $\{S_i\}$ from the first and second polarimetric images, the anterior segment retardance magnitude $\delta_C$ and orientation $\theta_C$ values that provide a minimum least-squares error fit of a Mueller equation; and means recorded on the recording medium for directing the ophthalmological system to compute a third polarimetric image of the retinal structure having a plurality of pixels $\{S(\delta_N, \theta_N)\}$ each corresponding to a first or second polarimetric image pixel $S(\delta_T, \theta_T)$ from which the effects of the anterior segment retardance are removed.

20. The computer program product of claim 19 further comprising:

means recorded on the recording medium for directing the ophthalmological system to compute, for a plurality of pixels $\{S_i\}$ from the first and second polarimetric images, the anterior segment retardance magnitude $\delta_C$ and orientation $\theta_C$ values and the retinal structure retardance magnitude $\{\delta_{Ni}\}$ and orientation $\{\theta_{Ni}\}$ values that provide a minimum least-squares error fit of $$M_T(\delta_T, \theta_T) = M_F(\delta_F, \theta_F) M_C(\delta_C, \theta_C) M_{2N}(2\delta_N, \theta_N) M_C(\delta_C, \theta_C) M_F(\delta_F, \theta_F).$$

* * * * *